United States Patent
Murayama

(10) Patent No.: US 9,615,724 B2
(45) Date of Patent: Apr. 11, 2017

(54) FLUID CONTROL APPARATUS FOR ENDOSCOPE

(71) Applicant: OLYMPUS CORPORATION, Tokyo (JP)

(72) Inventor: Masahiko Murayama, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/791,740

(22) Filed: Jul. 6, 2015

(65) Prior Publication Data
US 2015/0305599 A1    Oct. 29, 2015

Related U.S. Application Data

(63) Continuation of application No. PCT/JP2014/061173, filed on Apr. 21, 2014.

(30) Foreign Application Priority Data

Aug. 27, 2013    (JP) .................................. 2013-175922

(51) Int. Cl.
*A61B 1/12*        (2006.01)
*A61M 1/00*    (2006.01)
(Continued)

(52) U.S. Cl.
CPC ...... *A61B 1/00068* (2013.01); *A61B 1/00119* (2013.01); *A61B 1/015* (2013.01)

(58) Field of Classification Search
CPC ............ A61B 1/00094; A61B 1/00119; A61B 1/00128; A61B 1/00137; A61B 1/015; A61B 1/12; A61B 1/121; A61B 1/123; A61B 1/125–1/127; A61B 2090/701; G02B 27/0006
(Continued)

(56) References Cited

U.S. PATENT DOCUMENTS

2011/0071357 A1    3/2011  Ushijima

FOREIGN PATENT DOCUMENTS

EP          2335552 A1    6/2011
JP          S63-23637 A   1/1988
(Continued)

OTHER PUBLICATIONS

International Search Report dated Jul. 22, 2014 issued in PCT/JP2014/061173.
(Continued)

*Primary Examiner* — Ryan Henderson
(74) *Attorney, Agent, or Firm* — Scully, Scott, Murphy & Presser, P.C.

(57) ABSTRACT

A gas feeding duct, a suction duct, a first valve that is installed in the gas feeding duct and opens a flow passage only when gas feeding is underway, and a second valve that is installed in a part of the flow passage on an upstream side relative to the first valve, and opens the flow passage K along with gas feeding and closes the flow passage at least when suction is underway are included, and when neither gas feeding nor gas suctioning is underway, the second valve closes the flow passage in conjunction with the first valve unexpectedly opening the flow passage as a result of pressure variation in a part of the gas feeding duct on a downstream side relative to the first valve and thereby prevents reverse flow of a fluid to the upstream side relative to the second valve.

9 Claims, 17 Drawing Sheets

(51) Int. Cl.
*A61B 1/00* (2006.01)
*A61B 1/015* (2006.01)

(58) Field of Classification Search
USPC ............ 600/121–125, 153–159; 604/30–35, 604/99.01–99.03, 118–121
See application file for complete search history.

(56) References Cited

FOREIGN PATENT DOCUMENTS

| | | |
|---|---|---|
| JP | H02-172435 A | 7/1990 |
| JP | 2002-000557 A | 1/2002 |
| JP | 4608606 B2 | 1/2011 |
| WO | WO 2010/116563 A1 | 10/2010 |

OTHER PUBLICATIONS

Japanese Office Action dated Nov. 25, 2014 issued in JP 2014-547617.

FLUID CONTROL APPARATUS FOR ENDOSCOPE

CROSS REFERENCE TO RELATED APPLICATION

This application is a continuation application of PCT/JP2014/061173 filed on Apr. 21, 2014 and claims benefit of Japanese Application No. 2013-175922 filed in Japan on Aug. 27, 2013, the entire contents of which are incorporated herein by this reference.

BACKGROUND OF THE INVENTION

1. Field of the Invention

The present invention relates to a fluid control apparatus for an endoscope, the fluid control apparatus being provided on an endoscope and switching between supply of a gas to and suction of a fluid from an inside of a subject.

2. Description of the Related Art

In recent years, endoscopes have been widely used in a medical field. Endoscopes used in the medical field each enable an organ in a body cavity, which is a subject, to be observed by inserting an elongated insertion portion into the subject. Also, as necessary, various treatments can be performed using a treatment instrument inserted inside a treatment instrument insertion channel included in the endoscope.

Also, a configuration in which in addition to the aforementioned insertion channel, e.g., a forward water feeding duct for supplying a liquid to an inside of a subject and a gas/water feeding duct that feeds a liquid or a gas to an objective lens provided in a distal end face of a distal end in an insertion direction (hereinafter simply referred to as "distal end") of an insertion portion are provided in an endoscope is known. A configuration in which the insertion channel is used as a suction duct for sucking a fluid such as a liquid, which is, e.g., a body fluid, or a gas in a subject is also known.

Furthermore, in order to achieve reduction in diameter of the insertion portion, an endoscope configuration in which only one duct is provided in an endoscope to feed a gas to an inside of a subject or suck a fluid from the inside of the subject using the one endoscope duct is known. As examples of endoscopes whose insertion portion has a very small diameter, endoscopes used in the otorhinolaryngological field are known.

Japanese Patent No. 4608606 discloses a configuration in which one endoscope duct is provided in an insertion portion and an operation portion provided so as to be continuous with the insertion portion at a proximal end in an insertion direction (hereinafter simply referred to as "proximal end") of the insertion portion and a fluid control apparatus that switches between feeding of a gas to an inside of a subject or suction of a fluid from the inside of the subject using the one endoscope duct is provided on the operation portion.

FIG. 9 is a partial cross-sectional diagram schematically illustrating a conventional fluid control apparatus together with a gas feeding apparatus, a suction apparatus and an endoscope duct. Also, FIG. 10 is a cross-sectional diagram schematically illustrating a state in which a gas is supplied from the gas feeding apparatus in FIG. 9 using a gas feeding duct and the endoscope duct, according to switching control performed by the fluid control apparatus. Furthermore, FIG. 11 is a cross-sectional diagram schematically illustrating a state in which a fluid is sucked by the suction apparatus in FIG. 9 using a suction duct and the endoscope duct, according to switching control performed in the fluid control apparatus.

More specifically, as illustrated in FIG. 9, in Japanese Patent No. 4608606, a fluid control apparatus 500 provided on an operation portion of an endoscope includes a piston 501 including a gas feeding fitting 511, and a syringe 502 including a suction fitting 512. Also, the fluid control apparatus 500 includes an elastic member 503 including a suction leak hole 503h, and a button member 504.

A gas feeding apparatus 543 is connected to the gas feeding fitting 511 via a gas feeding tube 521. Note that a flow passage 501i inside the piston 501, a flow passage 511i inside the gas feeding fitting 511 and a flow passage 521i inside the gas feeding tube 521 communicate with a flow passage 505i of an endoscope duct 505 provided in an insertion portion and the operation portion of the endoscope.

Also, the flow passage 501i and the flow passage 511i provide a flow passage K of a gas feeding duct L in the fluid control apparatus 500, which supplies a gas A fed from the gas feeding apparatus 543 to the inside of the subject. In other words, the piston 510 and the gas feeding fitting 511 provide the gas feeding duct L in the fluid control apparatus 500.

In the flow passage 501i, a first valve 551 that closes the flow passage 501i when the fluid control apparatus 500 is not operated and a second valve 552 that opens the flow passage 501i are provided.

The first valve 551 functions as a check valve that prevents reverse flow of a fluid R to a part of the flow passage K on the upstream side relative to the first valve 551, and as illustrated in FIG. 10, is configured so as to open the flow passage K only when the gas A is fed from the gas feeding apparatus 543.

The second valve 552 is fixed to the piston 501 and formed integrally with a button member 504 exposed at an outer surface of the fluid control apparatus 500.

Also, as illustrated in FIG. 11, the second valve 552 is configured so as to, when suction from the inside of the subject is underway, close the flow passage 501i upon the second valve 552 being depressed by an operator together with the button member 504.

Also, the second valve 552 is configured so as to close the suction leak hole 503h upon the second valve 552 being depressed by the operator. Furthermore, the second valve 552 has a function that pushes the piston 501 down, thereby bringing the flow passage 505i and a flow passage V of a suction duct, which will be described later, into communication with each other.

Also, as illustrated in FIG. 9, a suction apparatus 533 is connected to the suction fitting 512 via a suction tube 522. Note that a flow passage 512i inside the suction fitting 512 communicates with a flow passage 522i of the suction tube 522 and is included in the flow passage V of the suction duct in the fluid control apparatus 500.

The syringe 502 covers an outer periphery of the distal end side in an extension direction Z of the piston 501 with a gap from the outer periphery, and in the gap, a flow passage 502i included in the flow passage V in the fluid control apparatus 500, which communicates with the flow passages 512i and 522i, is formed.

In other words, the syringe 502 and the suction fitting 512 provide a suction duct W in the fluid control apparatus 500.

Note that when the fluid control apparatus 500 is not operated, the flow passage V is occluded by a region provided at the distal end of the piston 501 and thereby is not in communication with the flow passage 505i, but in communication with an outside of the fluid control apparatus 500 via the suction leak hole 503*h* of the elastic member 503. Also, as stated above, the flow passage V communicates with the flow passage 505*i* only when the second valve 552 is pushed down.

According to the above, first, when the gas A is supplied to the inside of the subject using the flow passage K, the gas feeding apparatus 543 is driven, and then the gas A is introduced from the gas feeding apparatus 543 to the flow passage 511*i* via the flow passage 521*i*. Subsequently, as illustrated in FIG. 10, the gas A brings the first valve 551 into an open state from a closed state. Subsequently, the gas A is introduced to the flow passage 501*i* and supplied to the inside of the subject via the flow passage 505*i*.

Note that in this case, even if the suction apparatus 533 is driven, the flow passage V is not in communication with the flow passage 505*i* but is in communication with the outside of the fluid control apparatus 500 via the suction leak hole 503*h*. Therefore, the suction apparatus 533 sucks atmospheric air T via the suction leak hole 503*h* and the flow passage V.

Next, when a fluid R in the subject is sucked using the flow passage 505*i* and the flow passage V, as illustrated in FIG. 11, the second valve 552 is pushed down together with the button member 504, whereby the flow passage 501*i* and the suction leak hole 503*h* are closed and the piston 501 is pushed down via the second valve 552.

Consequently, the flow passage V comes into a non-communication state with the outside of the fluid control apparatus 500 but comes into communication with the flow passage 505*i*, and thus, the fluid R in the subject is introduced from the flow passage 505*i* to the flow passage 502*i*. Subsequently, the fluid R is sucked to the suction apparatus 533 via the flow passages 512*i* and 522*i*.

In this case, the flow passage 501*i* is closed by the first valve 551 and the second valve 552, whereby the fluid R in the subject and parts of the flow passages 501*i* and 505*i* on the downstream side relative to the second valve 552 is prevented from reversely flowing to the upstream side relative to the second valve 552 via the flow passage K.

In the configuration of the fluid control apparatus 500 disclosed in Japanese Patent No. 4608606, during use of the endoscope with neither gas feeding nor suction performed, in the flow passage K and the flow passage 505*i*, a pressure in the part on the downstream side relative to the first valve may vary, more specifically, the pressure may decrease for some reason.

A specific example will be indicated below with reference to FIGS. 12 to 14. FIG. 12 is a cross-sectional diagram illustrating a state in which a fluid supply member is connected to a liquid feeding fitting that communicates with the endoscope duct in FIG. 9 and a liquid is fed to the flow passage of the endoscope duct. Also, FIG. 13 is a cross-sectional diagram illustrating a state in which the liquid supplied from the fluid supply member to the endoscope duct in FIG. 12 is switched to a gas and the first valve is thereby opened. Furthermore, FIG. 14 is a cross-sectional diagram illustrating a state in which the supply of the gas from the fluid supply member in FIG. 13 causes a fluid in the gas feeding duct to reversely flow to the upstream side relative to the first valve.

Here, the configuration of the fluid control apparatus disclosed in Japanese Patent No. 4608606 includes no configuration that supplies a liquid to the inside of the subject via the flow passage 505*i*. Therefore, when a liquid is supplied to the inside of the subject, as illustrated in FIG. 12, it can be contemplated that a liquid E is supplied using a syringe 590, which is a fluid supply member, via a fitting 530 that is provided in the operation portion and is in communication with the flow passage 505*i*.

Note that in the supply of the liquid E, as illustrated in FIG. 12, the liquid E and a fluid R containing a gas A remaining in the flow passage 501*i* reversely flow to the upstream side in the flow passage 501*i*. Here, the first valve 551 prevents the fluid R from reversely flowing to the upstream side relative to the first valve 551. Furthermore, with the liquid supply from the syringe 590, a pressure in the flow passage 501*i* increases, and the increase reaches a position just before the first valve 551.

However, since not only the liquid E but also a certain amount of the gas A are included in the syringe 590, as illustrated in FIG. 13, immediately after supply of all the liquid E in the syringe 590, the gas A in the syringe 590 is supplied to the flow passage 505*i*.

In this case, at the moment of change from the supply of the liquid E to the supply of the gas A, the pressure on the downstream side relative to the first valve 551 in the flow passages 505*i* and 501*i* decreases because of a difference in pressure between the liquid E and the gas A. Accordingly, with the pressure decrease, as illustrated in FIG. 13, the first valve 551 is unexpectedly opened and the gas A in the flow passage 511*i* enters the flow passage 501*i*.

Note that in this case, as a result of the decrease of the pressure in the flow passage 501*i*, the second valve 552 is pulled so as to close the flow passage 501*i*, but is prevented from closing the flow passage 501*i* by the gas A entered from the flow passage 511*i*. Therefore, the gas A enters the part of the flow passage 501*i* on the downstream side relative to the second valve 552.

Subsequently, as illustrated in FIG. 14, if the supply of the gas A from the syringe 590 to the flow passage 505*i* is continued, the pressure in the flow passage 501*i* increases again, whereby the first valve 551 operates to close the flow passage 501*i*. However, before the first valve 551 is completely closed, the fluid R remaining in the flow passages 501*i* and 505*i* reversely flows because of the pressure increase. As a result, the fluid R reversely flows to the upstream side relative to the first valve 551, that is, the flow passage 511*i* side.

As described above, leakage of the fluid R to the flow passage 511*i* side in the flow passage K prevents a liquid from being fed at a sufficient pressure to the inside of the subject via the flow passage 505*i*.

A case where supply of the liquid E from the syringe 590 to the flow passage 505*i* via the fitting 530 varies the pressure on the downstream side relative to the first valve 551 in the flow passages 501*i* and 505*i* and the first valve 551 thereby unintentionally opens the flow passage 501*i* has been described above with reference to FIGS. 12 to 14.

Note that as another case where the pressure on the downstream side relative to the first valve 551 in the flow passages 501*i* and 505*i* varies, first, a case where the second valve 552 is intermittently depressed a plurality of times to intermittently perform a suction operation a plurality of times via the flow passage 505*i* and the flow passage V using the suction apparatus 533 may be contemplated.

Also, a situation immediately after completion of a suction operation via the flow passage 505*i* and the flow passage V using the suction apparatus 533, which is performed as a result of the second valve 552 being depressed, may be contemplated.

Furthermore, a case where during observation of the inside of the subject by insertion of the insertion portion of the endoscope into the inside of the subject, the pressure on the downstream side relative to the first valve 551 in the flow passages 505i and 501i, which are in communication with the inside of the subject, decreases for some reason may be contemplated.

Accordingly, there has been a demand for a configuration that can reliably prevent reverse flow of the fluid R to the flow passage 511i.

SUMMARY OF THE INVENTION

A fluid control apparatus according to an aspect of the present invention is a fluid control apparatus for an endoscope, the fluid control apparatus being provided in an endoscope and switching between supply of a gas to and suction of a fluid from an inside of a subject, the fluid control apparatus including: a gas feeding duct that communicates with one endoscope duct provided in the endoscope, and feeds the gas to the inside of the subject; a suction duct that is communicable with the endoscope duct, and sucks the fluid in the subject, jointly with the endoscope duct, after the suction duct is brought into communication with the endoscope duct; a first valve that is installed at a position partway through a flow passage of the gas feeding duct, and opens the flow passage only when gas feeding is underway and thereby prevents reverse flow of the fluid in the gas feeding duct to a part on an upstream side of the flow passage of the gas feeding duct when no gas feeding is underway; and a second valve that is installed at a position partway through the flow passage of the gas feeding duct, the position being on the upstream side relative to the first valve, and opens the flow passage along with gas feeding and closes the flow passage at least when suction is underway, and when neither gas feeding nor gas suctioning is underway, closes the flow passage in conjunction with the first valve unexpectedly opening the flow passage as a result of pressure variation in parts of the gas feeding duct and the endoscope duct on a downstream side relative to the first valve, and thereby prevents reverse flow of the fluid to an upstream side relative to a position at which the flow passage is closed.

DETAILED DESCRIPTION OF THE PREFERRED EMBODIMENT

An embodiment of the present invention will be described below with reference to the drawings.

Figure 1:
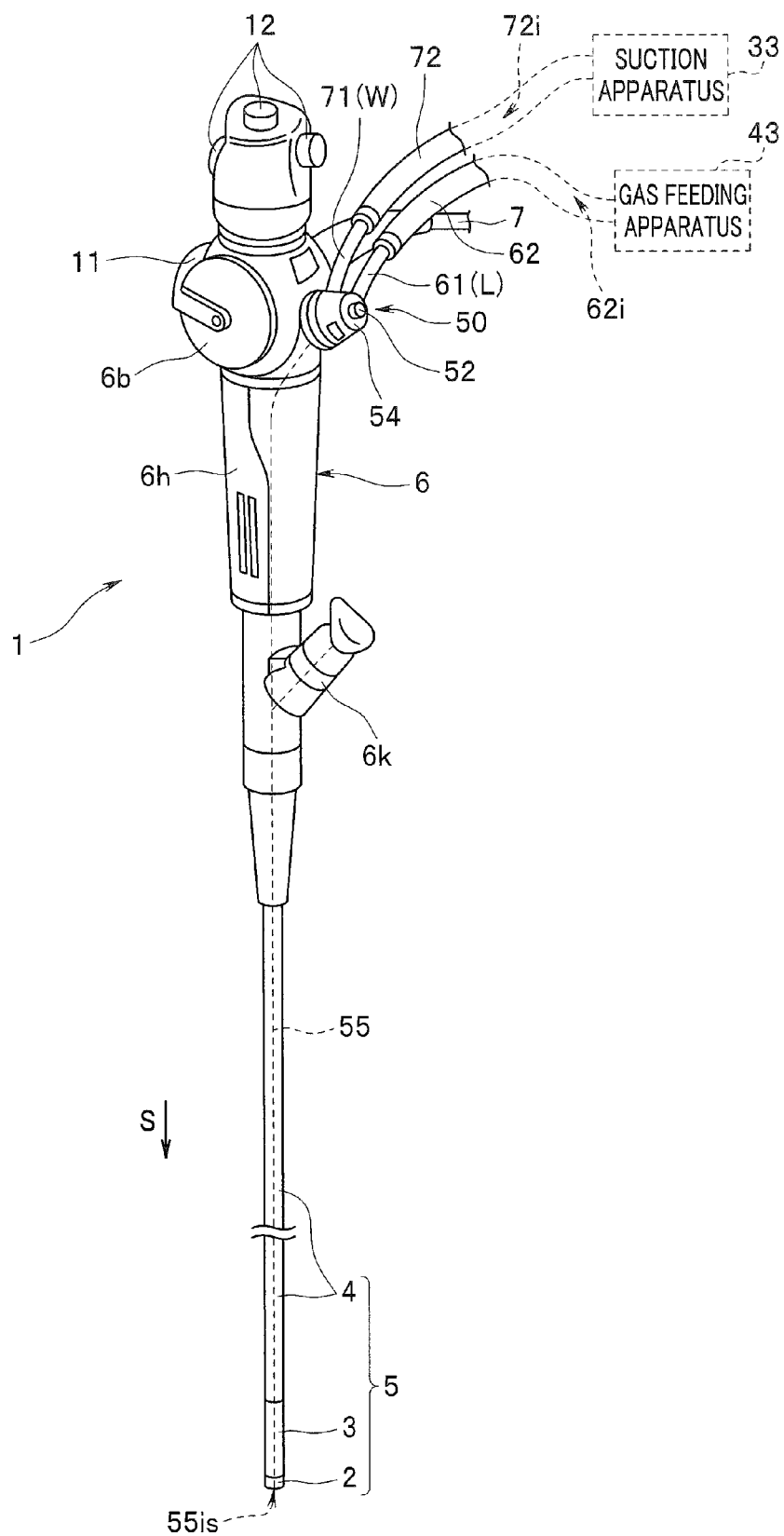
FIG. 1 is a diagram schematically illustrating an outer appearance of an endoscope with a fluid control apparatus for an endoscope according to the present embodiment provided thereon, together with a gas feeding apparatus and a suction apparatus.

FIG. 1 is a diagram schematically illustrating an outer appearance of an endoscope with a fluid control apparatus for an endoscope according to the present embodiment provided thereon, together with a gas feeding apparatus and a suction apparatus.

As illustrated in FIG. 1, the endoscope 1 includes an insertion portion 5 to be inserted to a subject, and an operation portion 6 provided so as to be continuous with a proximal end side in an insertion direction S (hereinafter simply referred to as "proximal end side") of the insertion portion 5.

The endoscope 1 also includes a universal cord 7 extending from the operation portion 6, and a non-illustrated connector provided at an extension end of the universal cord 7.

Note that the endoscope 1 is electrically connected to external apparatuses such as a control apparatus and an illumination apparatus via the connector.

The insertion portion 5 includes a distal end portion 2, a bending portion 3 and a flexible tube portion 4 in this order from the distal end side, and is formed in an elongated shape along the insertion direction S.

The bending portion 3 is bent in, for example, two directions as a result of a later-described bending lever 11 being turned and thereby changes an observation direction of a non-illustrated objective optical system provided in the distal end portion 2 or enhances insertability of the distal end portion 2 into a subject. The flexible tube portion 4 is provided so as to be continuous with the proximal end side of the bending portion 3.

A grasping portion 6*h* to be grasped by an operator is provided in the operation portion 6. Also, a fitting 6*k* is provided on the distal end side in an insertion direction S (hereinafter simply referred to as "distal end side") relative to the grasping portion 6*h* in the operation portion 6.

The fitting 6*k* communicates with a flow passage 55*i* (see FIG. 3) of a later-described endoscope duct 55 at a position on the downstream side relative to a communication enabling region D of a later-described flow passage 70*i* (see FIG. 3).

The fitting 6*k* provides a port of insertion/removal from/to the flow passage 55*i* when a treatment instrument is inserted/removed to/from a subject via the flow passage 55*i*, and also provides an attachment port to which a syringe 59 (see FIG. 2), which is a liquid supply member, is attached when a liquid E (see FIG. 6) is supplied to the inside of the subject via the flow passage 55*i*.

At an operation portion body 6*b* located on the proximal end side relative to the grasping portion 6*h* of the operation portion 6, a bending lever 11 for providing an instruction to bend the bending portion 3 in the two directions, and an operation switch 12 for providing an instruction for image pickup operation of a non-illustrated image pickup unit provided in the distal end portion 2 are provided.

Furthermore, on the operation portion body 6*b*, a fluid control apparatus for an endoscope (hereinafter simply referred to as "fluid control apparatus") 50 for switching between supply of a gas A (see FIG. 4) to the inside of a subject using the endoscope duct 55 and suction of a fluid R (see FIG. 5) from the inside of the subject using the endoscope duct 55 is provided.

Note that a configuration of the fluid control apparatus 50 will be described below with reference to FIGS. 2 to 5, 15, 16 and 17.

Figure 2:
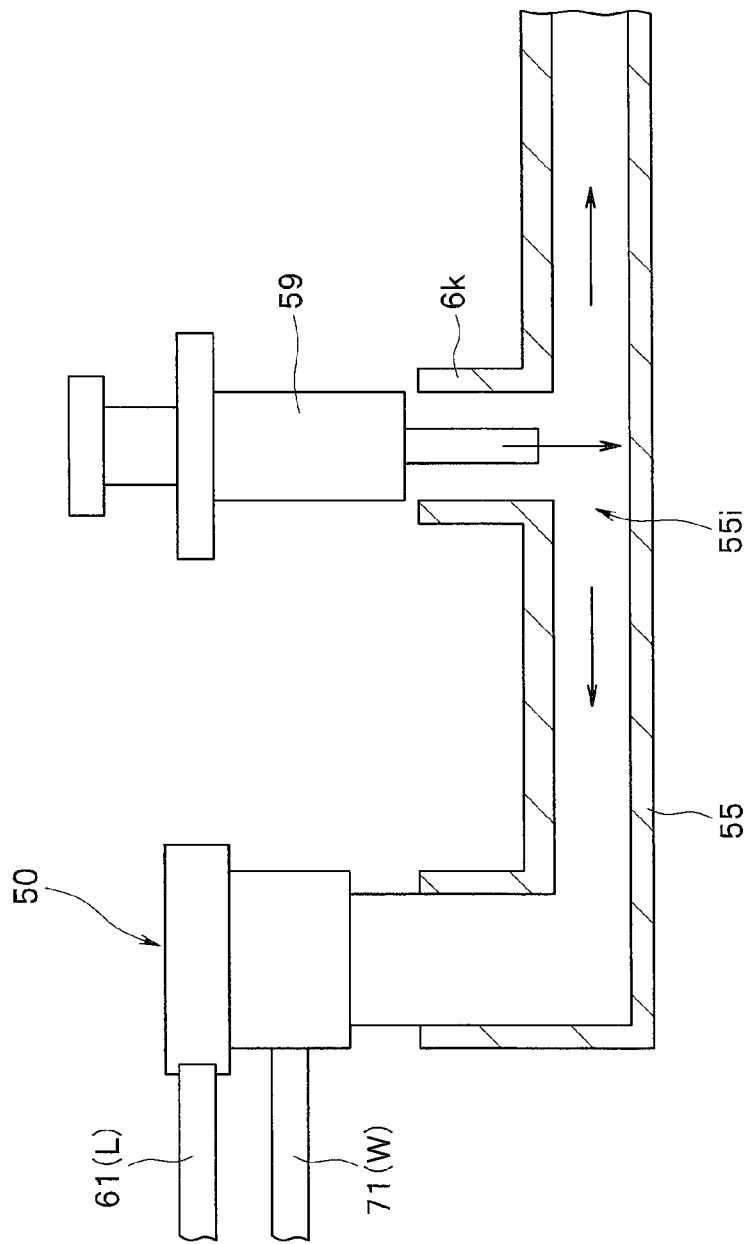
FIG. 2 is a partial cross-sectional diagram illustrating the fluid control apparatus in FIG. 1 together with an endoscope duct, a fitting that communicates with the endoscope duct, and a syringe attached to the fitting.

FIG. 2 is a partial cross-sectional diagram schematically illustrating the fluid control apparatus in FIG. 1 together with an endoscope duct, a fitting that communicates with the endoscope duct and a syringe attached to the fitting. Also, FIG. 3 is a partial cross-sectional diagram illustrating the fluid control apparatus in FIG. 2 together with the endoscope duct.

Figure 3:
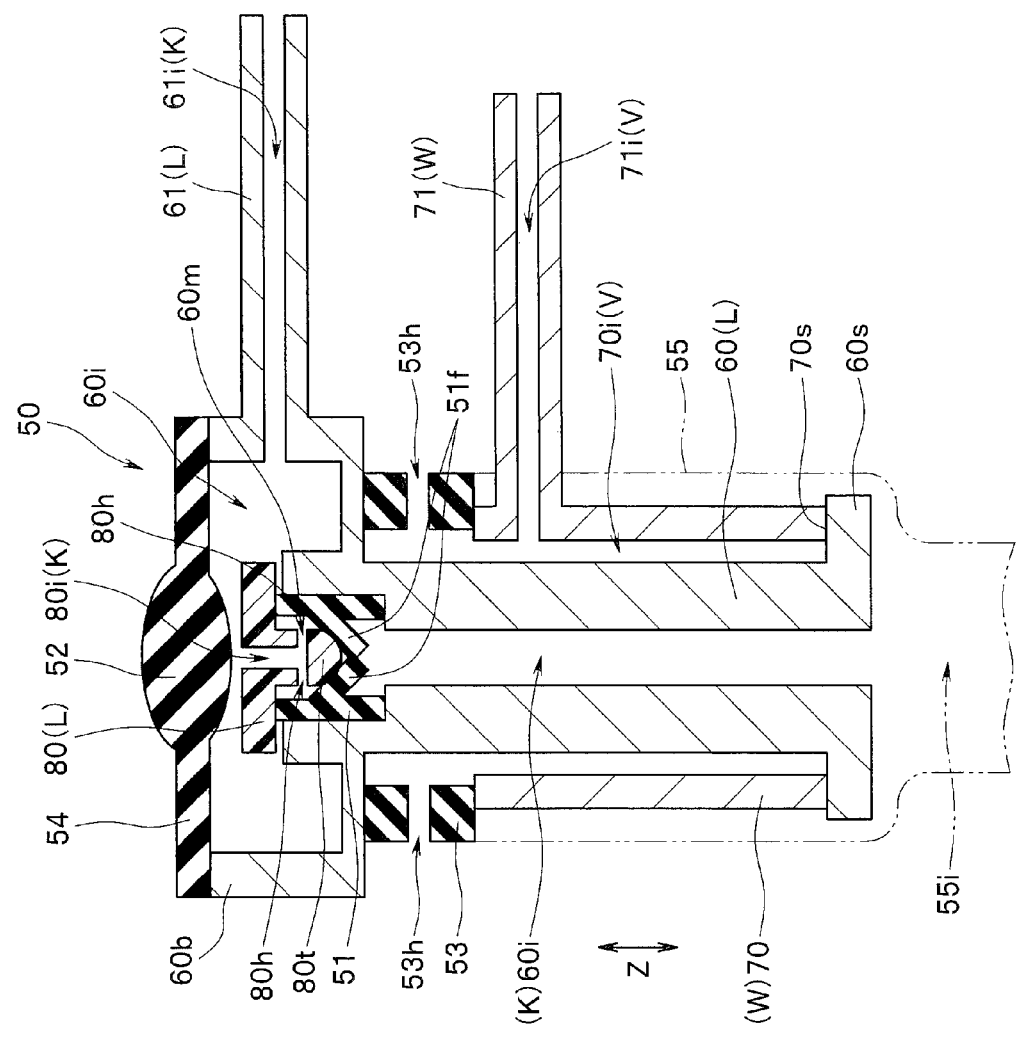
FIG. 3 is a partial cross-sectional diagram illustrating the fluid control apparatus in FIG. 2 together with the endoscope duct.
Figure 4:
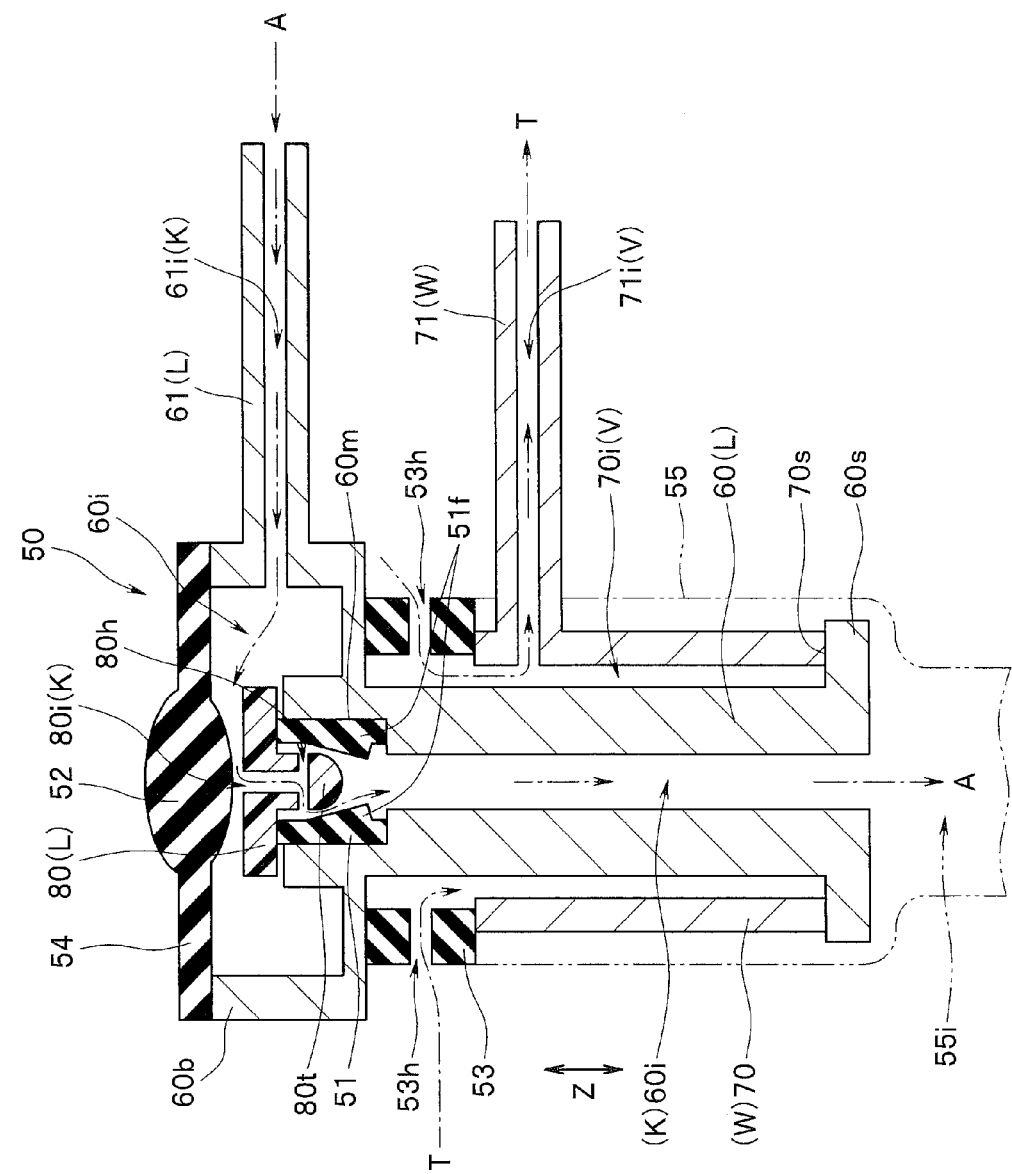
FIG. 4 is a cross-sectional diagram schematically illustrating a state in which a gas is supplied from the gas feeding apparatus in FIG. 3 using a gas feeding duct and the endoscope duct, according to switching control performed by the fluid control apparatus.
Figure 5:
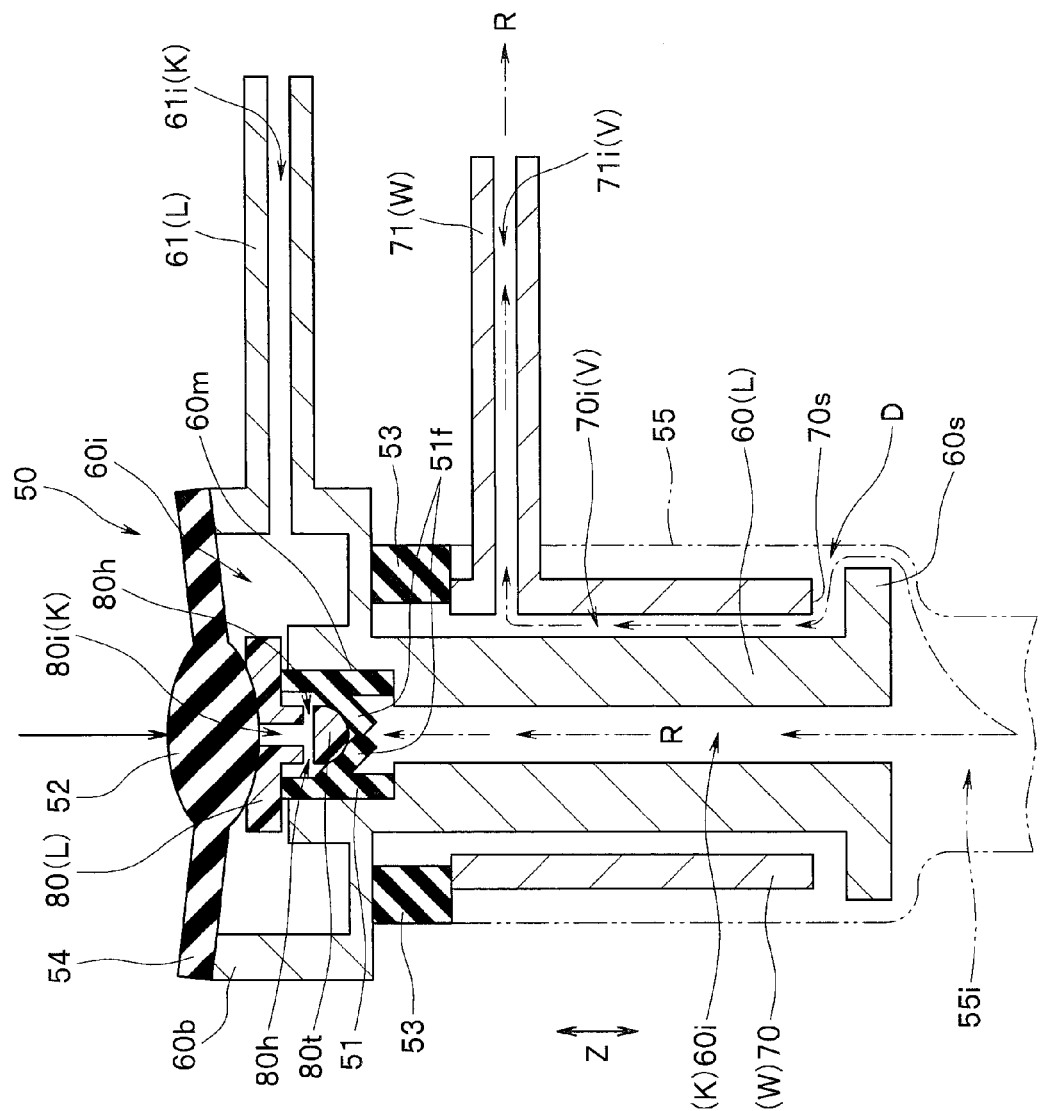
FIG. 5 is cross-sectional diagram schematically illustrating a state in which a fluid is sucked by the suction apparatus in FIG. 3 using the endoscope duct and a suction duct, according to switching control performed by the fluid control apparatus.

Furthermore, FIG. 4 is a cross-sectional diagram schematically illustrating a state in which a gas is supplied from the gas feeding apparatus in FIG. 3 using a gas feeding duct and the endoscope duct, according to switching control performed by the fluid control apparatus. Also, FIG. 5 is a cross-sectional diagram schematically illustrating a state in which a fluid is sucked by the suction apparatus in FIG. 3 using the endoscope duct and a suction duct, according to switching control performed by the fluid control apparatus.

Figure 15:
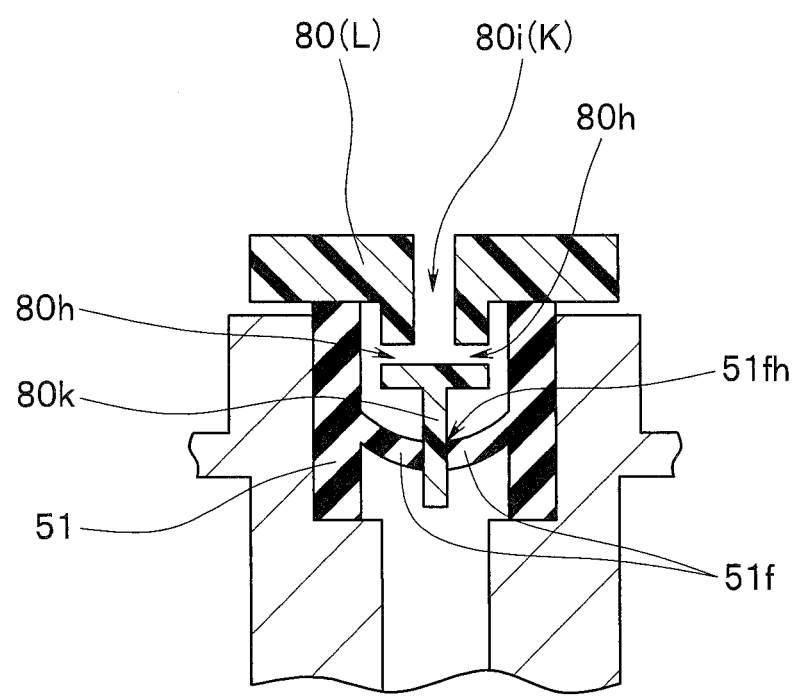
FIG. 15 is a partial cross-sectional diagram illustrating a modification in which a penetrating portion that penetrates a through hole formed in an inward flange portion that is in a closed state is formed in a valve seat in FIG. 3.

Furthermore, FIG. 15 is a partial cross-sectional diagram illustrating a modification in which a penetrating portion that penetrates a through hole formed in an inward flange portion that is in a closed state is formed in a valve seat in FIG. 3.

Figure 16:
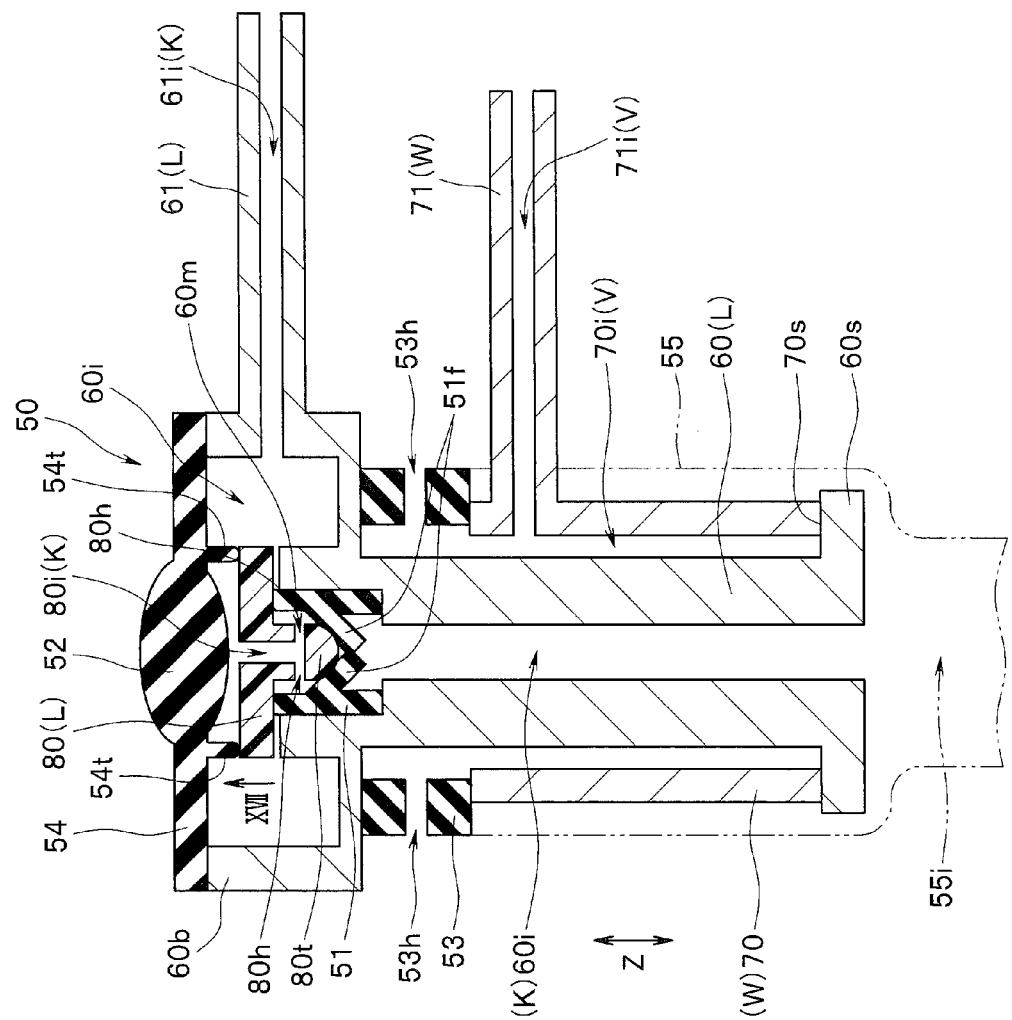
FIG. 16 is a partial cross-sectional diagram illustrating a modification in which a plurality of projections that abut a valve seat are provided in a button member in FIG. 3.
Figure 17:
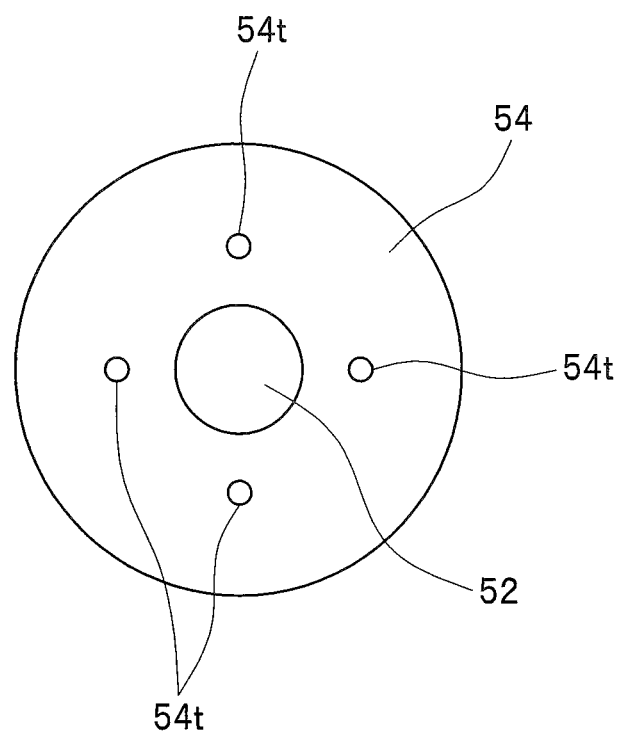
FIG. 17 is a bottom view of the button member in FIG. 16 in the XVII direction in FIG. 16.

Also, FIG. 16 is a partial cross-sectional diagram illustrating a modification in which a plurality of projections that abut a valve seat are provided in a button member in FIG. 3, and FIG. 17 is a bottom view of the button member in FIG. 16 in the XVII direction in FIG. 16.

As illustrated in FIGS. 1 and 2, one endoscope duct 55 is provided in the insertion portion 5 and the operation portion 6.

As illustrated in FIG. 1, a distal end 55*is* of the flow passage 55*i* of the endoscope duct 55 opens in a distal end face of the distal end portion 2. As illustrated in FIG. 2, a proximal end of the flow passage 55*i* is connected to the fluid control apparatus 50.

Also, as illustrated in FIG. 2, at a position partway through the flow passage 55*i*, as described above, the fitting 6*k* communicates with the flow passage 55*i* in the operation portion 6.

As illustrated in FIG. 3, a main portion of the fluid control apparatus 50 provided on the operation portion body 6*b* of the operation portion 6 of the endoscope 1 includes a piston 60 including a gas feeding fitting 61, a syringe 70 including a suction fitting 71, a rubber spring 53 including a suction leak hole 53*h*, and a button member 54.

Note that in the present embodiment, the gas feeding fitting 61 is formed integrally with the piston 60, but the gas feeding fitting 61 may be separate from the piston 60, and the suction fitting 71 is also formed integrally with the syringe 70, but the suction fitting 71 may be separate from the syringe 70.

As illustrated in FIG. 1, a gas feeding apparatus 43 is connected to the gas feeding fitting 61 via a gas feeding tube 62.

Note that a flow passage 61*i* inside the gas feeding fitting 61 and a flow passage 62*i* inside the gas feeding tube 62 communicate with a later-described in-piston flow passage (hereinafter simply referred to as "flow passage") 60*i* of the piston 60 and the flow passage 55*i* of the endoscope duct 55.

Also, the flow passage 61*i* provides, jointly with the flow passage 60*i*, a flow passage K of a gas feeding duct L in the fluid control apparatus 50, which supplies the gas A (see FIG. 4) fed from the gas feeding apparatus 43 to the inside of the subject via the flow passage 55*i*. In other words, the piston 60 and the gas feeding fitting 61 provides the gas feeding duct L in the fluid control apparatus 50.

Also, as illustrated in FIG. 3, at respective positions partway through the flow passage 60*i* of the piston 60, a first valve 51 and a second valve 52 are provided.

The first valve 51 is installed at the relevant position partway through the flow passage 60*i*. Also, as illustrated in FIG. 4, the first valve 51 opens the flow passage 60*i* only when gas feeding is underway using the gas feeding duct L, and thus functions as a check valve that prevents a fluid R in the flow passage K from reversely flowing to the upstream side relative to the first valve 51 when no gas feeding is underway.

More specifically, the first valve 51 is formed in a tubular shape including an openable/closable inward flange portion 51*f*, and fitted in a diameter-increased hole 60*m* included in the flow passage 60*i*, which is provided at a region facing the second valve 52 in an extension direction Z of the fluid control apparatus 50, in the piston 60.

Also, a valve seat 80 is fitted in the diameter-increased hole 60*m* together with the first valve 51. As illustrated in FIG. 3, the valve seat 80 includes an abutment portion 80*t* that abuts the inward flange portion 51*f* that is in a closed state. Note that as illustrated in FIG. 15, in the valve seat 80, a penetrating portion 80k that penetrates a through hole 51fh formed in the inward flange portion 51f that is in a closed state may be formed. Also, the configuration illustrated in FIG. 15 is applicable to all of the valve seats 80 illustrated in FIGS. 3 to 8.

Also, the valve seat 80 includes an in-valve seat flow passage (hereinafter simply referred to as "flow passage") 80i inside, the flow passage 80i communicating with the flow passage 60i, and a leakage hole 80h formed on the distal end side in the extension direction Z of the flow passage 80i. Note that the flow passage 80i is included in the flow passage K, and the valve seat 80 is included in the gas feeding duct L.

In the first valve 51, when the gas A is introduced from the gas feeding apparatus 43 to the flow passage 80i via the flow passage 62i, the flow passage 61i and a part of the flow passage 60i on the upstream side relative to the first valve 51, as illustrated in FIG. 4, the gas leaked from the leakage hole 80h opens the inward flange portion 51f. Accordingly, the first valve 51 is configured so as to open the flow passage 60i only when gas feeding is underway.

The second valve 52 is installed coaxially with the first valve 51 along the extension direction Z on the upstream side relative to the first valve 51, at the relevant position partway through the flow passage 60i, that is, in the flow passage 80i.

Also, the second valve 52 is formed integrally with the button member 54. The button member 54 is fixed to the piston 60 and is exposed at an outer surface of the fluid control apparatus 50.

Also, as illustrated in FIGS. 16 and 17, at a surface of the button member 54 that faces the valve seat 80, a plurality of projections 54t that abut the valve seat 80 and press the valve seat 80 against the first valve 51 in the extension direction Z may be provided so as to surround an outer periphery of the second valve 52.

Also, as illustrated in FIG. 4, the second valve 52 is configured so as to open the flow passage 60i by means of the gas A when gas feeding is underway using the gas feeding duct L, and close the flow passage 60i at least when suction is underway using a later-described suction duct W.

More specifically, as illustrated in FIG. 3, the second valve 52 is configured so as to open the flow passage 60i when a later-described operation to depress the button member 54 is not performed.

Note that the second valve 52 may be configured so as to close the flow passage 60i when the later-described operation to depress the button member 54 is not performed. The present embodiment will be described taking a case where the flow passage 60i is configured to be opened when the later-described operation to depress the button member 54 is not performed as an example.

Also, the second valve 52 is configured in the button member 54 that can be depressed in the extension direction Z by an operator, and, as illustrated in FIG. 5, is configured so as to close the flow passage 60i as a result of the operator depressing the button member 54 when suction from the inside of the subject is underway.

More specifically, the second valve 52 is configured so as to, when the second valve 52 is depressed by the operator together with the button member 54, closes the above-described flow passage 80i of the valve seat 80.

Note that as described above, the valve seat 80 occludes an opening at a part of proximal end of the diameter-increased hole 60m except the flow passage 80i.

Accordingly, when the flow passage 80i is closed by the second valve 52, the upstream side and the downstream side of the flow passage 60i with the second valve 52 therebetween are completely shut off from each other by the second valve 52.

Also, the second valve 52 is configured so as to squash and close the later-described suction leak hole 53h in the rubber spring 53 in the extension direction Z as a result of the second valve 52 being depressed by the operator.

The rubber spring 53 is located between a diameter-increased region 60b on the proximal end side in the extension direction Z of the piston 60 and a proximal end in the extension direction Z of the syringe 70 in the extension direction Z.

Furthermore, the second valve 52 has a function that when the piston 60 is pushed down in the extension direction Z, brings the flow passage 55i and a later-described flow passage V of the suction duct W into communication with each other.

Furthermore, when neither gas feeding nor gas suctioning is underway, the second valve 52 closes the flow passage 60i in conjunction with the first valve 51 unexpectedly opening the flow passage 60i as a result of the aforementioned pressure variation on the downstream side relative to the first valve 51 in the flow passage 60i of the gas feeding duct L and the flow passage 55i. Accordingly, the second valve 52 functions as a check valve that prevents the fluid R from reversely flowing to a part of the flow passage 60i on the upstream side relative to the second valve 52. Note that details of an operation of the second valve 52 closing in conjunction with unexpected release of the first valve 51 will be described later.

Also, the second valve 52 does not necessarily need to be provided coaxially with the first valve 51, and may be provided separately from the button member 54. In other words, the piston 60 may be pushed down by the button member 54. However, even in this case, the second valve 52 has a function that opens/closes the part of the flow passage 60i on the upstream side relative to the first valve 51.

As illustrated in FIGS. 4 and 5, the piston 60 can be moved in the extension direction Z by the second valve 52 being depressed.

Also, when no operation to depress the second valve 52 is performed by the operator, as illustrated in FIG. 3, the piston 60 maintains the flow passage 55i and the later-described flow passage 70i in the non-communication state with each other by means of a region 60s on the distal end side in the extension direction Z of the piston 60.

Also, the piston 60 is configured so that when the second valve 52 is depressed and the piston 60 is thereby moved to the distal end side in the extension direction Z, as illustrated in FIG. 5, the flow passage 55i comes into communication with the flow passage 70i at the communication enabling region D.

As illustrated in FIG. 1, a suction apparatus 33 is connected to the suction fitting 71 of the syringe 70 via a suction tube 72. Note that a flow passage 71i inside the suction fitting 71 communicates with a flow passage 72i of the suction tube 72, and is included in the flow passage V of the suction duct W in the fluid control apparatus 50.

The syringe 70 covers an outer periphery on the distal end side in the extension direction Z of the piston 60 with a gap from the outer periphery, and in the gap, the flow passage 70i included in the flow passage V of the fluid control apparatus 50, which communicates with the flow passage 71i and the flow passage 72i, is formed. In other words, the syringe 70 and the suction fitting 71 provide the suction duct W.

Note that when the fluid control apparatus 50 is not operated by the operator, the flow passage V is not in communication with the flow passage 55$i$ because the region 60$s$ on the distal end side of the piston 60 abuts the distal end 70$s$ in the extension direction Z of the syringe 70, and the flow passage V is thereby occluded by the distal end-side region 60$s$ and is in communication with the outside of the fluid control apparatus 50 via the suction leak hole 53$h$ of the rubber spring 53.

Also, as described above, only when the second valve 52 is pushed down, the flow passage V comes into communication with the flow passage 55$i$ as a result of the distal end 70$s$ of the syringe 70 being spaced from the distal end-side region 60$s$ at the communication enabling region D.

Accordingly, first, when the gas A is supplied to the inside of the subject using the flow passage K, as illustrated in FIG. 4, the gas A introduced from the gas feeding apparatus 43 to the flow passage 61$i$ via the flow passage 62$i$ after driving of the gas feeding apparatus 43 is introduced to the part of the flow passage 60$i$ on the upstream side relative to the second valve 52. In this case, when the second valve 52 is closed, the gas A brings the second valve 52 into an open state.

Subsequently, the gas A is further introduced to the flow passage 80$i$ and leaks from the flow passage 80$i$ via the leakage hole 80$h$, and thereby brings the inward flange portion 51$f$ of the first valve 51 from a closed state to an open state. In other words, the gas A brings the first valve 51 from a closed state into an open state.

Subsequently, the gas A flows to a part of the flow passage 60$i$ on the downstream side relative to the first valve 51, and is further introduced to the flow passage 55$i$ and supplied from the distal end 55$is$ to the inside of the subject via the flow passage 55$i$.

Note that if the gas feeding apparatus 43 is consistently driven, a non-illustrated gas feeding leak hole may be provided in the part of the flow passage 60$i$ on the upstream side relative to the first valve 51 to allow the gas A to consistently leak from the gas feeding leak hole to the outside of the fluid control apparatus 50 when the gas A is not fed to the inside of the subject, and supply the gas A to the first valve 51 side only when the gas feeding leak hole is occluded by the operator.

Also, when gas feeding is underway, even if the suction apparatus 33 is driven, as illustrated in FIG. 4, the flow passage V is not in communication with the flow passage 55$i$ but is in communication with the outside of the fluid control apparatus 50 via the suction leak hole 53$h$, and thus, the suction apparatus 33 sucks atmospheric air T via the suction leak hole 53$h$ and the flow passage V.

Next, when the fluid R in the subject is sucked using the flow passage 55$i$ and the flow passage V, as illustrated in FIG. 5, the second valve 52 is pushed down along the extension direction Z, together with the button member 54.

Consequently, the flow passage 80$i$ is closed by the second valve 52, and the rubber spring 53 is squashed in the extension direction Z and the suction leak hole 53$h$ is closed. Furthermore, the piston 60 is pushed down along the extension direction Z via the second valve 52.

Consequently, the flow passage 55$i$ is brought into the non-communication state with the gas feeding apparatus 43 by the second valve 52, and the flow passage V is brought into the non-communication state with the outside of the fluid control apparatus 50 but into communication with the flow passage 55$i$ at the communication enabling region D. Accordingly, the fluid R inside the subject is introduced from the flow passage 55$i$ to the flow passage 70$i$ and sucked to the suction apparatus 33 via the flow passage 71$i$ and the flow passage 72$i$.

In this case, along with the suction, the suction pressure may cause the first valve 51 to open the flow passage 60$i$; however, the flow passage 80$i$ is closed by the second valve 52, preventing the fluid R in the subject and the parts of the passages 60$i$ and 55$i$ on the downstream side relative to the second valve 52 from reversely flowing to the upstream side relative to the second valve 52 via the flow passage K.

Figure 6:
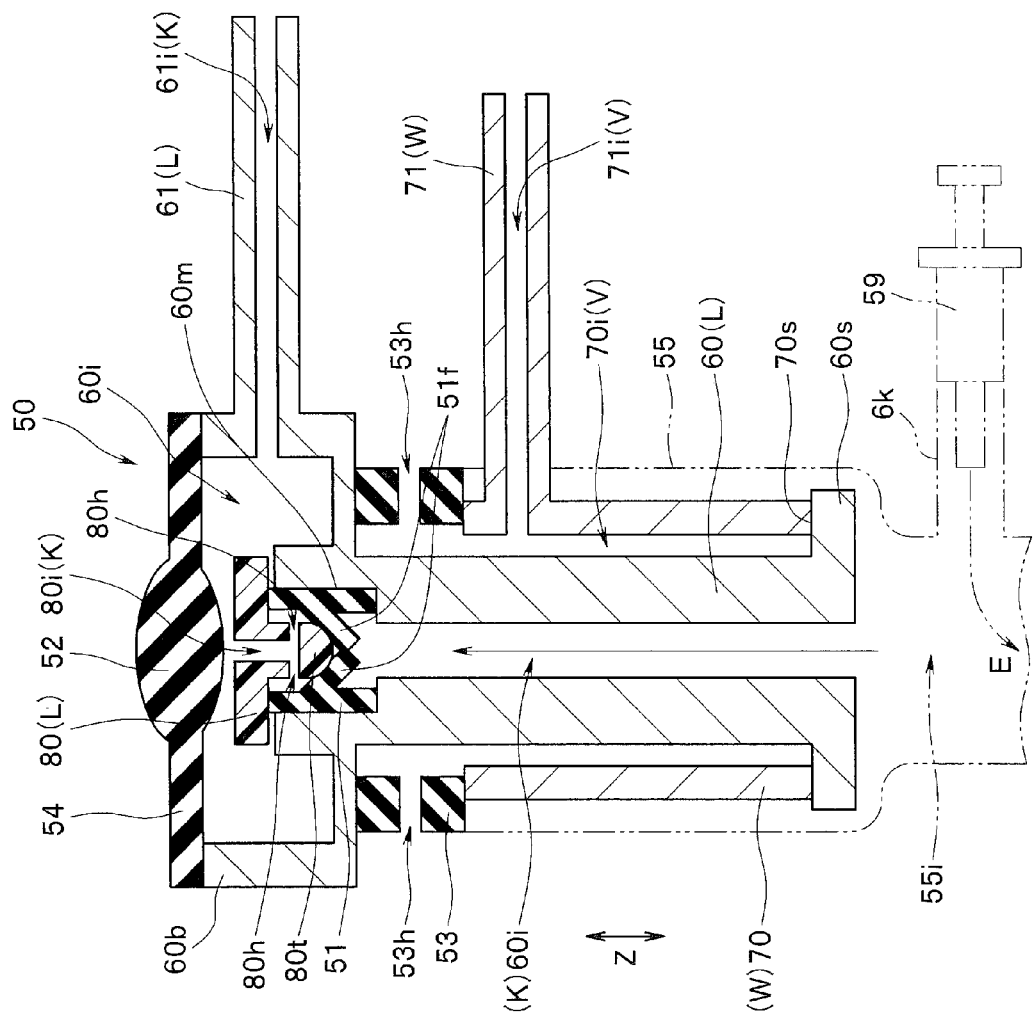
FIG. 6 is a cross-sectional diagram illustrating a state in which a fluid supply member is connected to a liquid feeding fitting that communicates with the endoscope duct in FIG. 3 and a liquid is fed to a flow passage of the endoscope duct.
Figure 7:
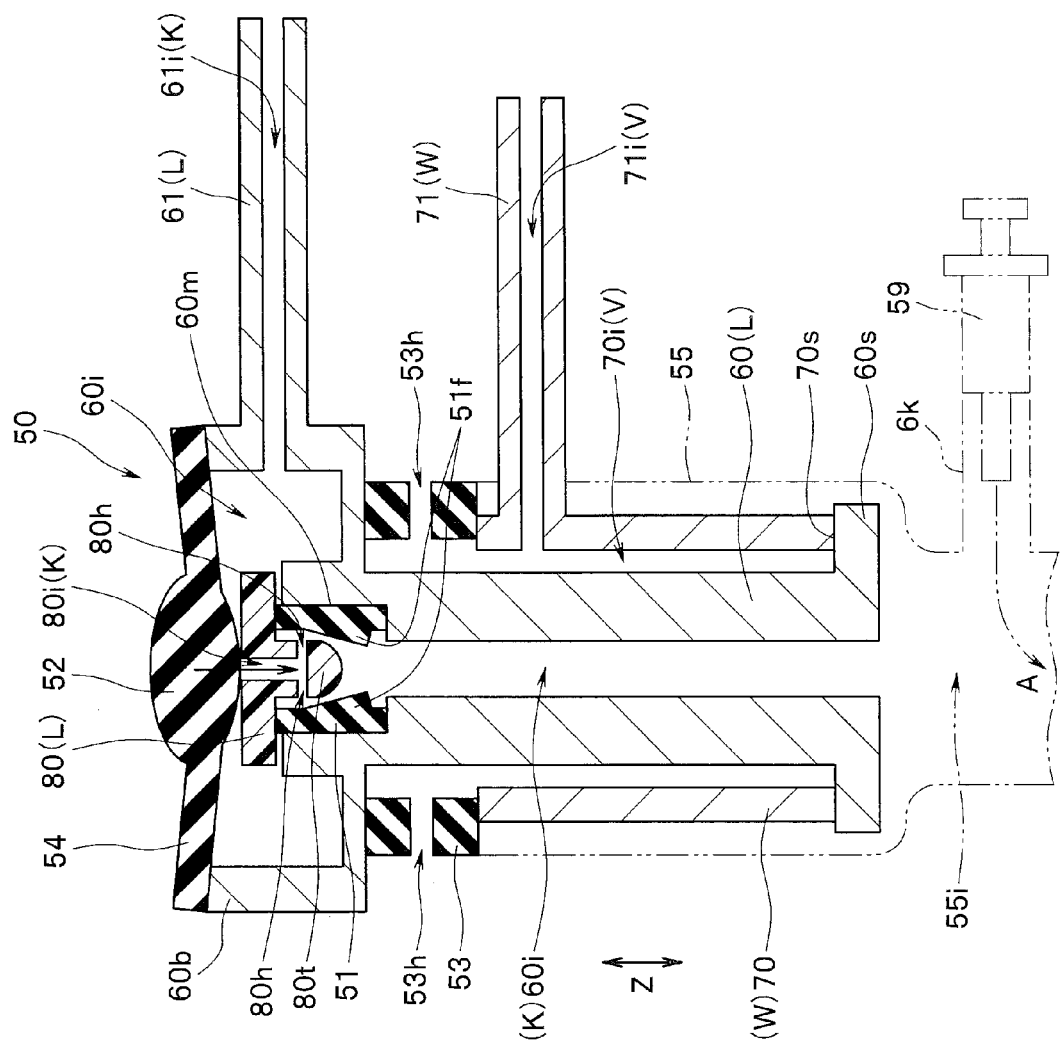
FIG. 7 is a cross-sectional diagram illustrating a state in which the liquid supplied from the fluid supply member to the endoscope duct in FIG. 6 is switched to a gas and a second valve is closed in conjunction with a first valve opening.
Figure 8:
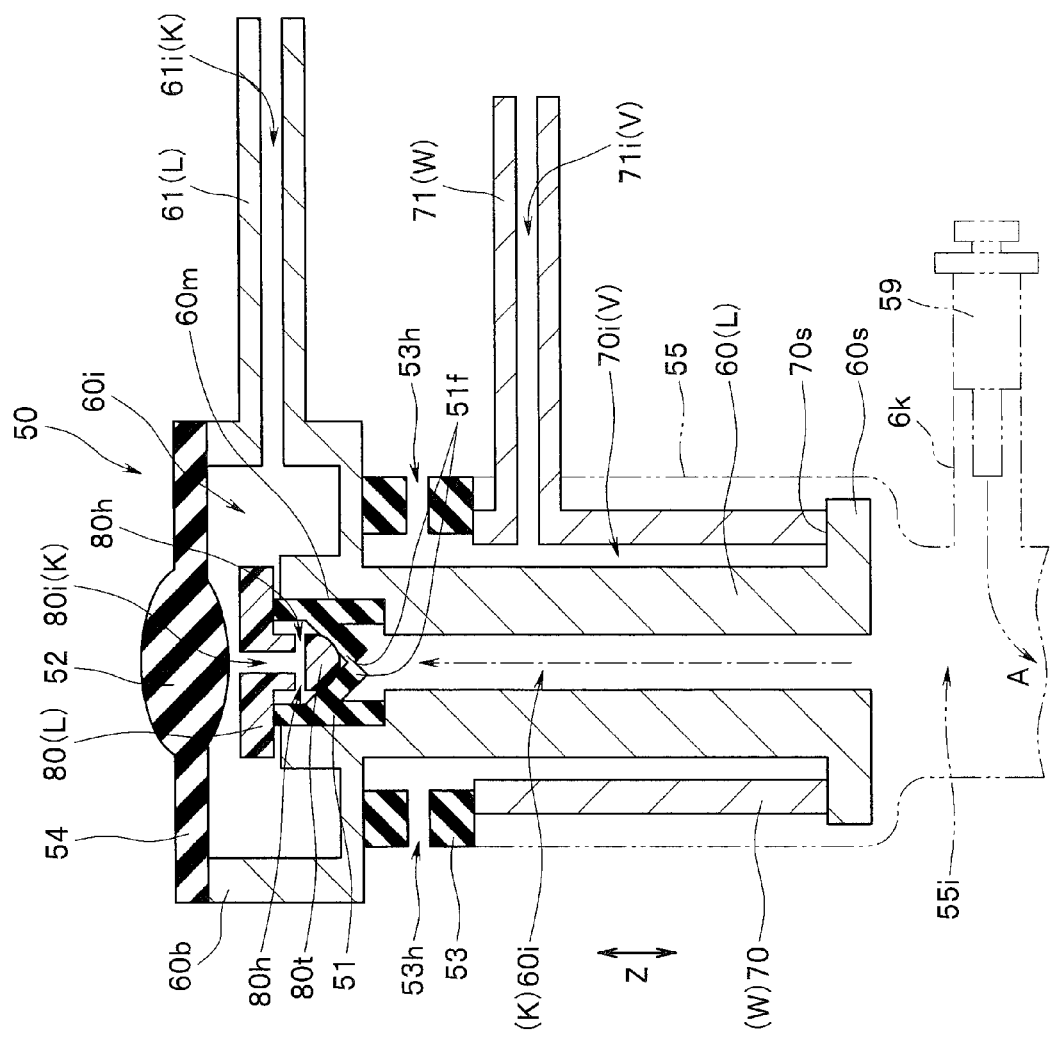
FIG. 8 is a cross-sectional diagram illustrating a state in which the first valve is closed by supply of the gas from the fluid supply member in FIG. 7.
Figure 9:
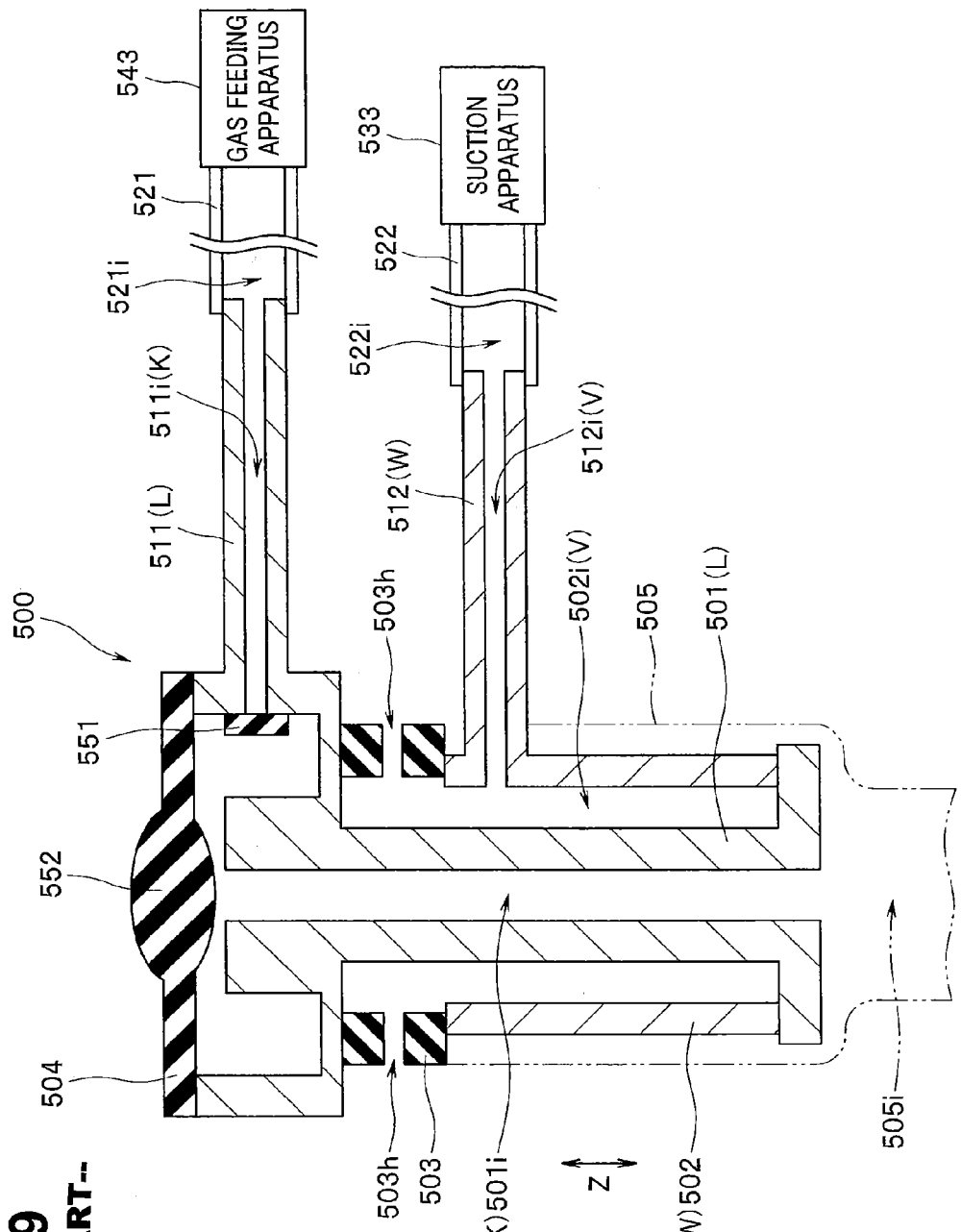
FIG. 9 is a partial cross-sectional diagram schematically illustrating a conventional fluid control apparatus together with a gas feeding apparatus, a suction apparatus and an endoscope duct.
Figure 10:
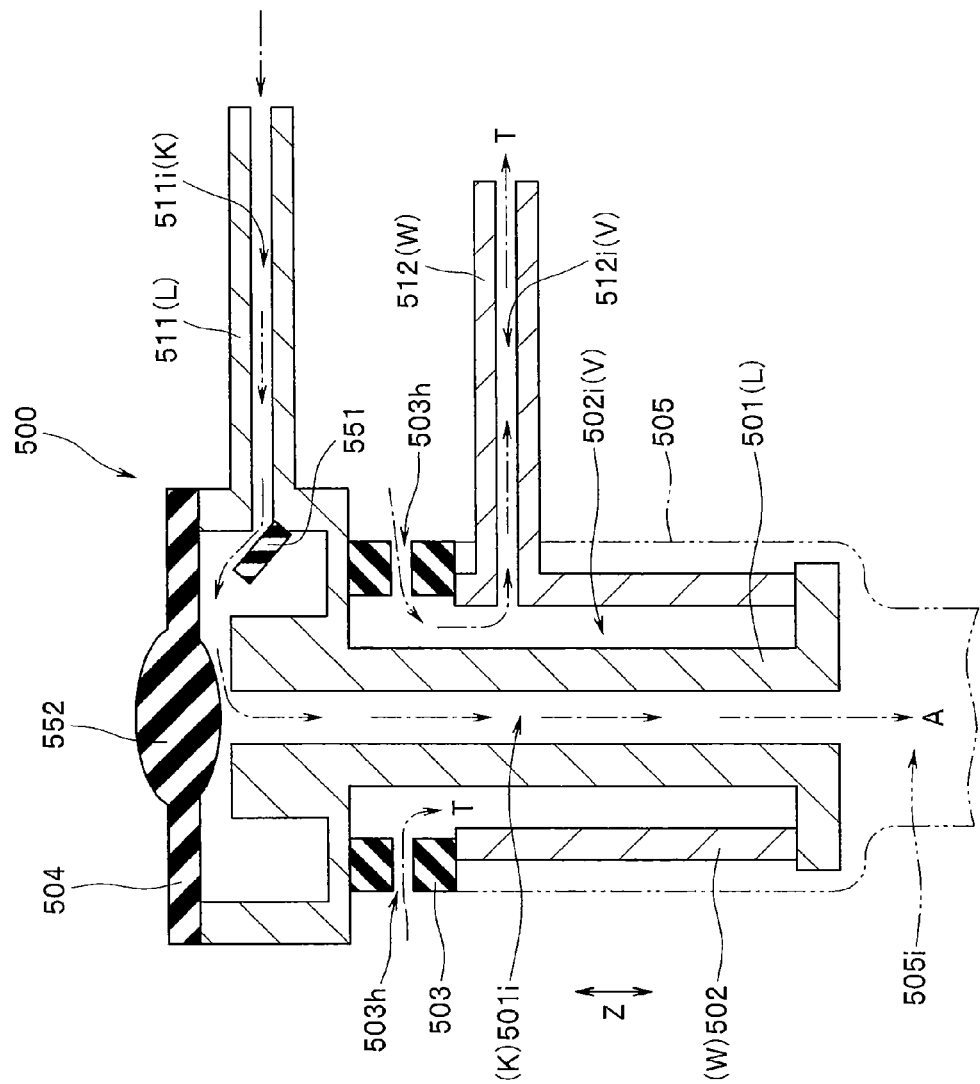
FIG. 10 is a cross-sectional diagram schematically illustrating a state in which a gas is supplied from the gas feeding apparatus in FIG. 9 using a gas feeding duct and the endoscope duct, according to switching control performed by the fluid control apparatus.
Figure 11:
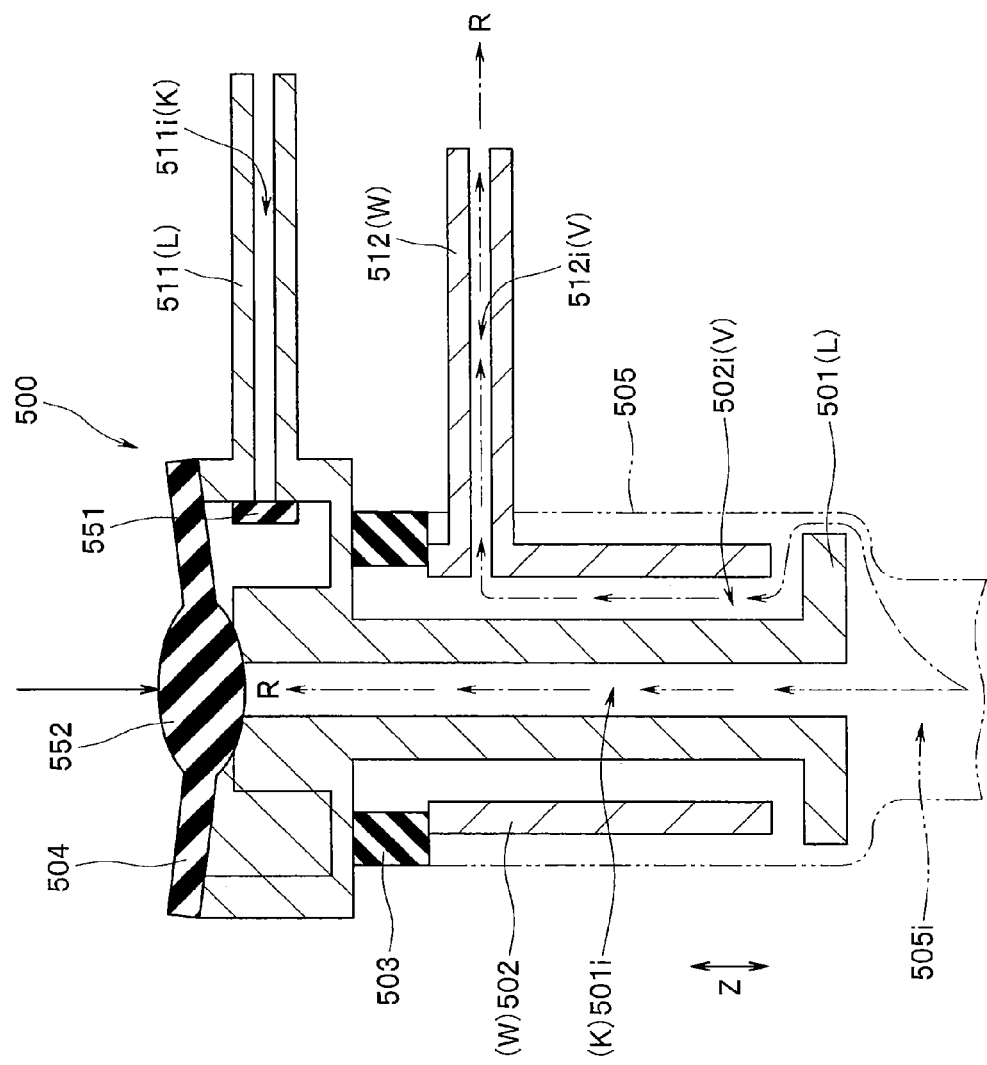
FIG. 11 is a cross-sectional diagram schematically illustrating a state in which a fluid is sucked by the suction apparatus in FIG. 9 using a suction duct and the endoscope duct, according to switching control performed by the fluid control apparatus.
Figure 12:
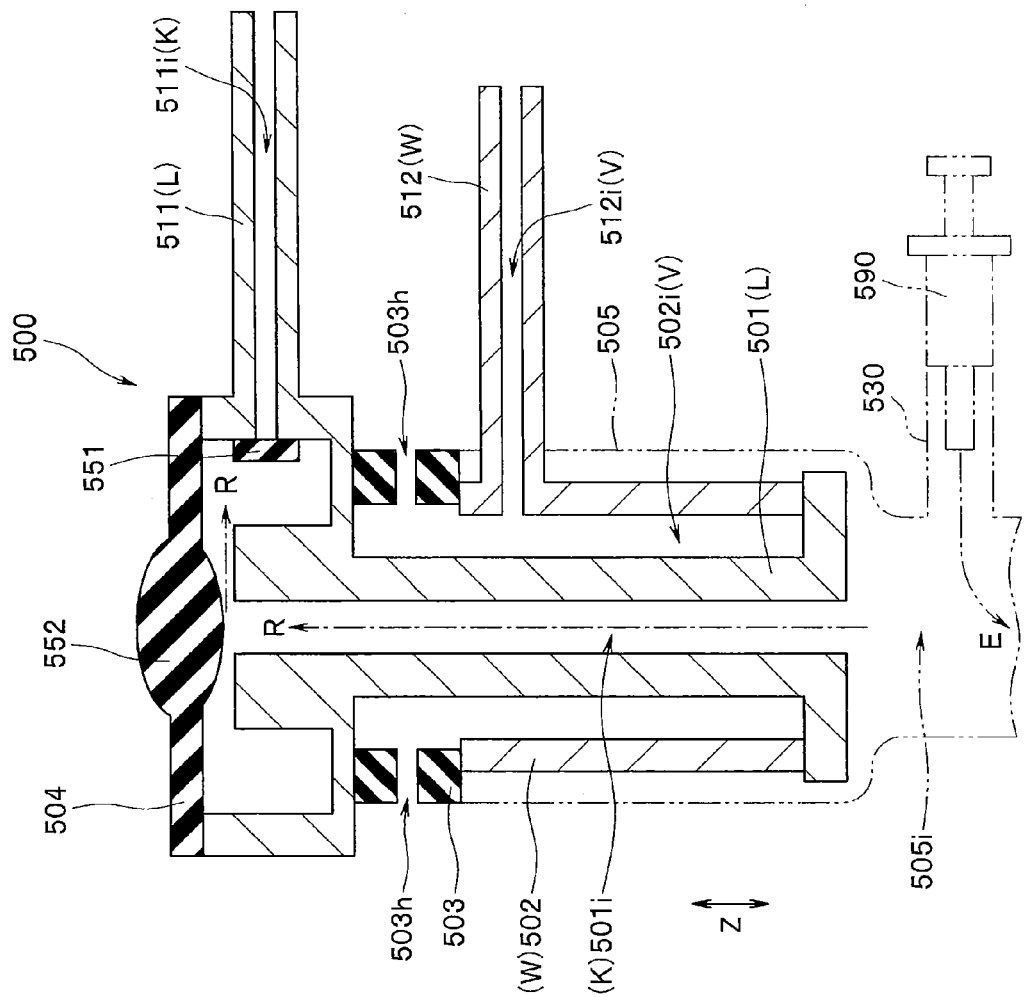
FIG. 12 is a cross-sectional diagram illustrating a state in which a fluid supply member is connected to a liquid feeding fitting that communicates with the endoscope duct in FIG. 9 and a liquid is fed to a flow passage of the endoscope duct.

Next, an operation of the second valve that prevents the fluid R from reversely flowing to the part of the flow passage K on the upstream side relative to the second valve 52 by the second valve 52 closing the flow passage 60$i$ in conjunction with the first valve 51 unexpectedly opening the flow passage 60$i$ as a result of pressure variation on the downstream side relative to the first valve 51 in the flow passages 60$i$ and 55$i$ when neither gas feeding nor gas suctioning is underway will be described with reference to FIGS. 6 to 8.

FIG. 6 is a cross-sectional diagram illustrating a state in which a fluid supply member is connected to a liquid feeding fitting that communicates with the endoscope duct in FIG. 3 and a liquid is fed to the flow passage of the endoscope duct. Also, FIG. 7 is a cross-sectional diagram illustrating a state in which the second valve is closed in conjunction with the first valve opening as a result of the liquid supplied from the fluid supply member to the endoscope duct in FIG. 6 being switched to a gas. Furthermore, FIG. 8 is a cross-sectional diagram illustrating a state in which the first valve is closed by supply of the gas from the fluid supply member in FIG. 7.

Note that as a case where pressure variation occurs on the downstream side relative to the above-described first valve 51 in the flow passages 55$i$ and 60$i$, a case where a liquid E is supplied from the syringe 59 to the flow passage 55$i$ via the fitting 6$k$ will be indicated below as an example.

The configuration of the fluid control apparatus 50 according to the present embodiment includes no configuration that supplies a liquid E to the inside of the subject via the flow passage 55$i$.

Therefore, when the liquid E is supplied to the inside of the subject, as illustrated in FIGS. 6 to 8, supplying the liquid E to the inside of the subject using the syringe 59 attached to the fitting 6$k$ provided in the operation portion 6, the fitting 6$k$ communicating with the flow passage 55$i$, can be contemplated.

Note that in the supply of the liquid E, as illustrated in FIG. 6, the liquid E and a fluid R containing a gas A remaining in the flow passage 55$i$ reversely flow to the upstream side in the flow passages 55$i$ and 60$i$, but the fluid R is prevented from reversely flowing to the upstream side relative to the first valve 51, by the first valve 51.

Furthermore, along with the liquid feeding from the syringe 59, a pressure in the flow passage 55$i$ and the part of the flow passage 60$i$ on the downstream side relative to the first valve 51 increases, and the increase reaches a position just before the first valve 51.

Also, in this case, the pressure increase may cause the valve seat 80 to float from the first valve body 51 to the button member 54 side.

However, as illustrated in FIGS. 16 and 17, if the plurality of projections 54$t$ in button member 54 that press the valve seat 80 against the first valve body 51 in the extension direction Z are provided, the valve seat 80 is prevented from floating from the first valve body 51 along with the liquid feeding from the syringe 59.

Subsequently, immediately after supply of all the liquid E in the syringe 59, not only the liquid E, but also a certain amount of the gas A are included in the syringe 59, and thus, as illustrated in FIG. 7, the gas A in the syringe 59 is supplied to the flow passage 55i.

In this case, the pressure in the flow passage 55i and the part of the flow passage 60i on the downstream side relative to the first valve 51 decreases at a moment of change from the supply of the liquid E to supply of the gas A because of a difference in pressure between the liquid E and the gas A, and along with the pressure decrease, as illustrated in FIG. 7, the first valve 51 unexpectedly opens.

However, along with the above-described pressure decrease, the second valve 52 located on the upstream side relative to the first valve 51 closes the flow passage 80i in conjunction with the first valve 51 opening.

Accordingly, as opposed to the conventional technique, originally, no force is exerted to urge the gas A in the flow passage 61i to enter the downstream side relative to the second valve 52, preventing a closing operation of the second valve 52 from being hindered by the gas A, as opposed to the conventional technique.

Subsequently, as illustrated in FIG. 8, if the supply of the gas A from the syringe 59 to the flow passage 55i is continued, the pressure in the flow passage 55i and the part of the flow passage 60i on the downstream side relative to the first valve 51 increases again, whereby the first valve 51 operates to close the flow passage 60i.

Therefore, the fluid R remaining in the flow passage 55i and the part of the flow passage 60i on the downstream side relative to the first valve 51 is prevented from reversely flowing to the upstream side relative to the first valve 51.

However, even with the configuration according to the present embodiment, as with the conventional technique, the fluid R remaining in the flow passage 55i and the part of the flow passage 60i on the downstream side relative to the first valve 51 may reversely flow because of the pressure increase before the first valve 51 is completely closed, resulting in the fluid R entering the flow passage 80i.

Regarding such problem, as illustrated in FIG. 7, in the configuration according to the present embodiment, the flow passage 80i is reliably closed by the second valve 52, and thus, even if the fluid R enters the flow passage 80i, the fluid R is prevented from reversely flowing to the upstream side relative to the second valve 52.

Note that as illustrated in FIG. 8, the second valve 52 opens the flow passage 80i after the first valve 51 closes the flow passage 60i.

Also, in order to more reliably prevent the fluid R from reversely flowing to the upstream side relative to the second valve 52, as described above, a configuration of a modification in which when the button member 54 is not operated, the second valve 52 closes the flow passage 80i, which is contrary to that of the present embodiment illustrated in FIG. 3, is preferable.

As the above-described case where pressure variation occurs on the downstream side relative to the first valve 51 in the flow passage K, the case where a liquid E is supplied from the syringe 59 to the flow passage 55i via the fitting 6k has been indicated above as an example with reference to FIGS. 6 to 8.

The above-described case where pressure variation occurs on the downstream side relative to the first valve 51 in the flow passages 55i and 60i is not limited to this case, but may be a case where a suction operation using suction apparatus 33 via the flow passage 55i and the flow passage V is intermittently performed a plurality of times by the second valve 552 being intermittently depressed a plurality of times as described above.

Also, the case may be a situation immediately after completion of a suction operation via the flow passage 55i and the flow passage V using the suction apparatus 33, which is performed by the second valve 52 being depressed.

Furthermore, the case may also be a case where during observation of an inside of a subject by inserting the insertion portion 5 of the endoscope 1 into the inside of the subject, the pressure on the downstream side relative to the first valve 51 decreases in the flow passages 55i and 60i that communicate with the inside of the subject, for some reason.

As described above, in the present embodiment, it has been indicated that in the gas feeding duct L, the second valve 52 that closes the flow passage K of the gas feeding duct L at least when suction is underway is provided on the upstream side relative to the first valve 51 that prevents reverse flow of a fluid R. In other words, it has been indicated that the arrangement of the first valve 51 and the second valve 52 is contrary to the conventional arrangement of the first valve 551 and the second valve 552.

Figure 13:
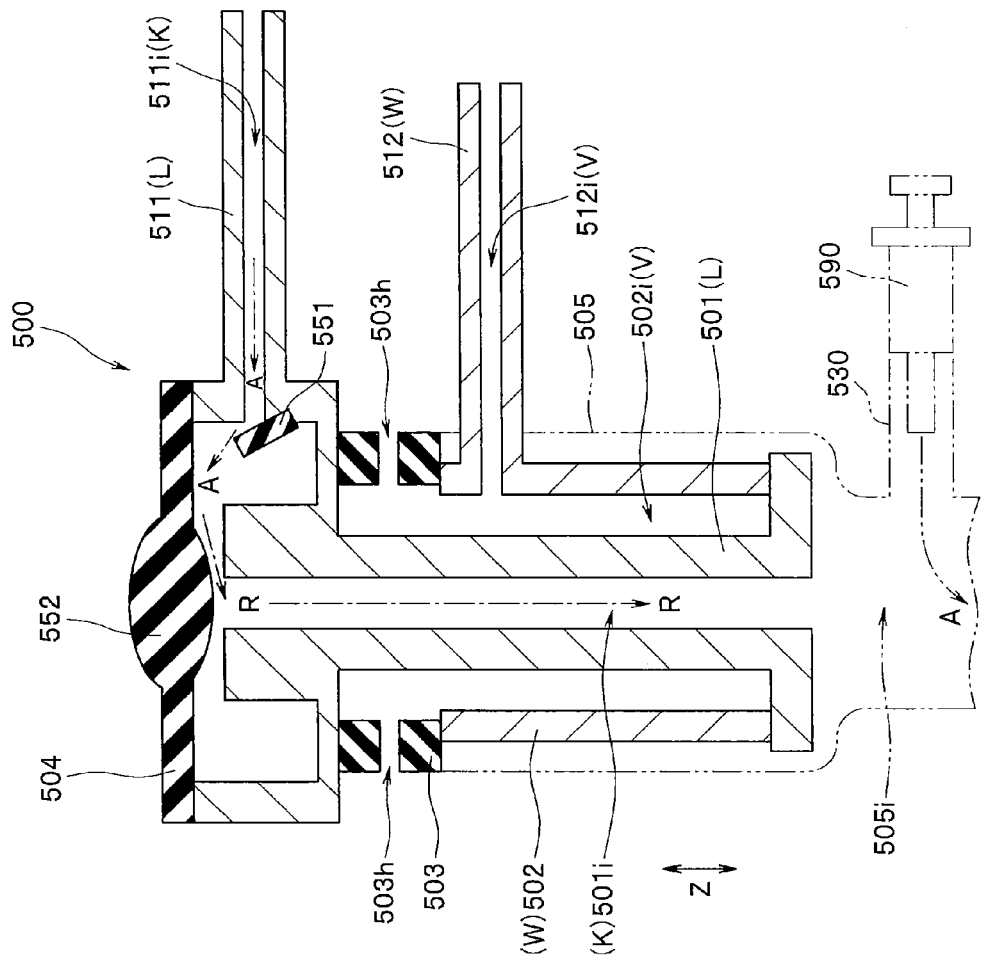
FIG. 13 is a cross-sectional diagram illustrating a state in which the liquid supplied from the fluid supply member to the endoscope duct in FIG. 12 is switched to a gas and the first valve is thereby opened.
Figure 14:
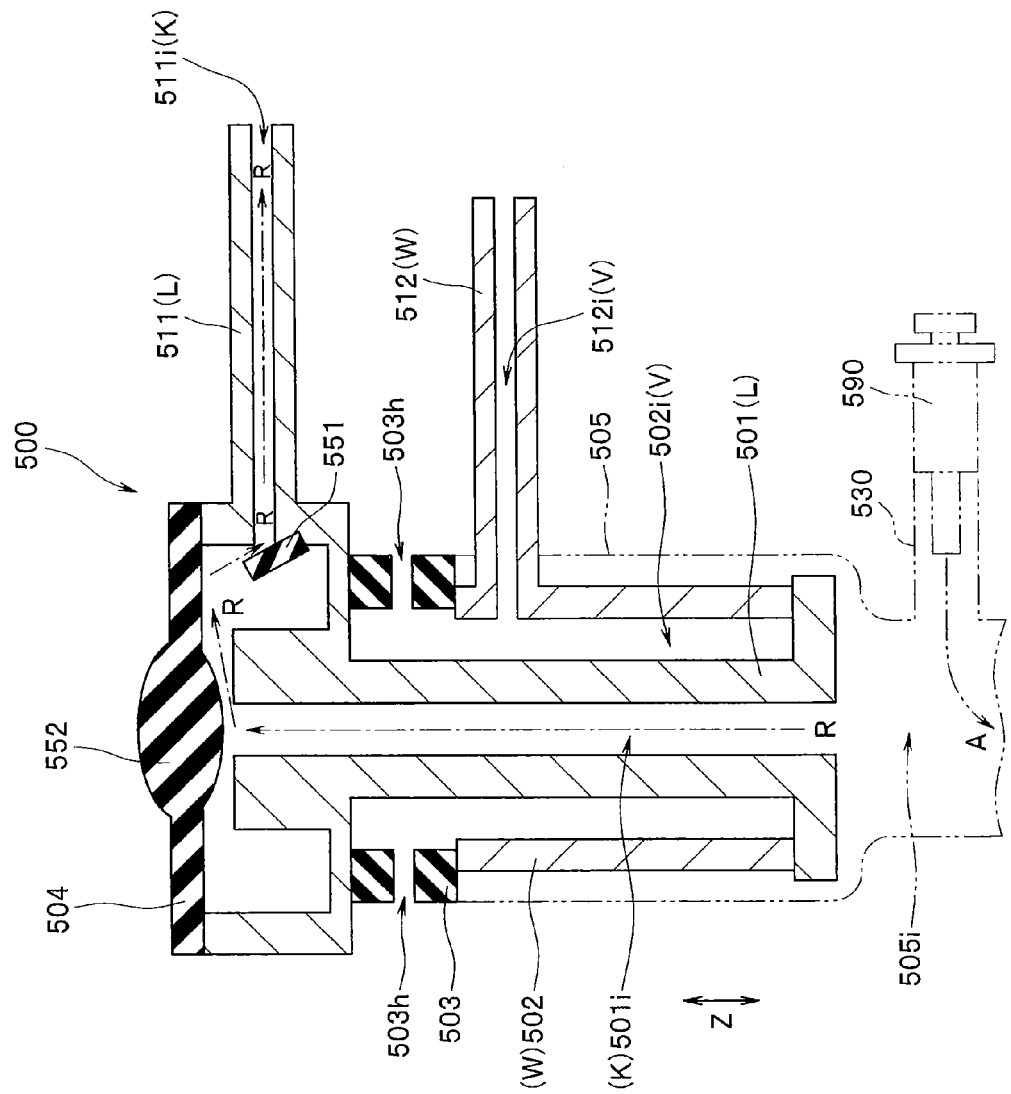
FIG. 14 is a cross-sectional diagram illustrating a state in which the supply of the gas from the fluid supply member in FIG. 13 causes the fluid in the gas feeding duct to reversely flow to the upstream side relative to the first valve.

Therefore, there is the conventional problem that if pressure variation occurs, more specifically, if the pressure decreases, on the downstream side relative to the first valve 51 in the flow passages when neither gas feeding nor gas suctioning is underway, as illustrated in FIGS. 13 and 14, the first valve 551 unexpectedly opens along with the pressure decrease, resulting in a fluid R remaining in the flow passage 501i reversely flowing to the flow passage 511i side before the first valve 551 is completely closed.

Also, there has been the conventional problem that when the fluid R reversely flows, the second valve 552 operates to open the flow passage 501i and thus fails to function as a check valve.

However, in the present embodiment, where pressure variation occurs, more specifically, where the pressure decreases, on the downstream side relative to the first valve 51 in the flow passages 55i and 60i when neither gas feeding nor gas suctioning is underway, even if the first valve 51 unexpectedly opens along with the pressure decrease as illustrated in FIG. 7, the second valve 52 located on the upstream side relative to the first valve 51 closes the flow passage 80i in conjunction with the first valve 51 opening along with the above-described pressure decrease.

Therefore, even if a fluid R remaining in the flow passage 55i and the part of the flow passage 60i on the downstream side relative to the first valve 51 is urged to reversely flow by a pressure increase before the first valve 51 is completely closed, the fluid R is prevented from reversely flowing on the upstream side relative to the second valve 52, by the second valve 52 that functions as a check valve only in this case.

According to the above, a fluid control apparatus 50 that, in a configuration in which fluid supply and suction can be performed using one endoscope duct 55 provided in an endoscope, can reliably prevent a fluid from reversely flowing to a part of a gas feeding duct K, which communicates with the endoscope duct 55, on the upstream side relative to a valve provided in the gas feeding duct K, the valve functioning as a check valve, can be provided.

What is claimed is:

1. A fluid control apparatus for an endoscope, the fluid control apparatus being provided in an endoscope and switching between supply of a gas to and suction of a fluid from an inside of a subject, the fluid control apparatus comprising:

a gas feeding duct that communicates with one endoscope duct provided in the endoscope, and feeds the gas to the inside of the subject;

a suction duct that is communicable with the endoscope duct, and sucks the fluid in the subject, jointly with the endoscope duct, after the suction duct is brought into communication with the endoscope duct;

a first valve that is installed at a position partway through a flow passage of the gas feeding duct, the first valve opening the flow passage by a feeding pressure of the gas only when gas feeding is underway and closing the flow passage when no gas feeding is underway to thereby prevent reverse flow of the fluid in the gas feeding duct to a part on an upstream side of the flow passage of the gas feeding duct when no gas feeding is underway; and a second valve that is installed at a position partway through the flow passage of the gas feeding duct, the position being on the upstream side relative to the first valve, the second valve always opening the flow passage when gas feeding is underway and closing the flow passage at least when suction is underway in a state where the suction duct communicates with the endoscope duct, and the second valve being configured to automatically close the flow passage in a case where the first valve opens the flow passage as a result of a pressure decrease in parts of the gas feeding duct and the endoscope duct on a downstream side relative to the first valve, the second valve automatically closing the flow passage as a result of the pressure decrease to thereby prevent reverse flow of the fluid to the upstream side relative to a position at which the flow passage is closed when no gas feeding is underway in a state where the gas feeding duct does not communicate with the endoscope duct and no gas suctioning is underway in a state where the suction duct does not communicate with the endoscope duct, wherein the second valve is configured by a depressible button.

2. A fluid control apparatus for an endoscope according to claim 1, wherein the second valve opens the flow passage when no operation to depress the second valve is performed, and closes the flow passage when an operation to depress the second valve is performed.

3. A fluid control apparatus for an endoscope according to claim 1, wherein the second valve closes the flow passage when no operation to depress the second valve is performed.

4. A fluid control apparatus for an endoscope according to claim 1, further comprising a piston that is movable along with an operation to depress the second valve, wherein when no operation to depress the second valve is performed, a flow passage of the endoscope duct and a flow passage of the suction duct are maintained in a non-communication state with each other by the piston, and when the second valve is depressed and the piston is thereby moved, the flow passage of the suction duct comes into communication with the flow passage of the endoscope duct.

5. The fluid control apparatus for an endoscope according to claim 4, wherein:

the piston includes an in-piston flow passage inside, the in-piston flow passage communicating with the flow passage of the gas feeding duct and being included in the flow passage of the gas feeding duct; and the first valve and the second valve are provided on the in-piston flow passage.

6. The fluid control apparatus for an endoscope according to claim 5, wherein:

the first valve is formed in a tubular shape having an openable/closable inward flange portion;

on the in-piston flow passage, a valve seat including an abutment portion that abuts the inward flange portion that is in a closed state or a penetrating portion that penetrates a through hole formed in the inward flange portion that is in a closed state, the valve seat including, inside, an in-valve seat flow passage that communicates with the in-piston flow passage and is included in the flow passage of the gas feeding duct, and a leakage hole formed in the in-valve seat flow passage is provided; and when gas feeding is underway, the gas leaked from the leakage hole via the in-valve seat flow passage opens the inward flange portion, whereby the flow passage of the gas feeding duct is opened by the first valve.

7. The fluid control apparatus for an endoscope according to claim 6, wherein when an operation to depress the second valve is performed, the second valve closes the in-valve seat flow passage and thereby closes the flow passage of the gas feeding duct.

8. The fluid control apparatus for an endoscope according to claim 5, wherein the first valve and the second valve are coaxially provided on the in-piston flow passage.

9. The fluid control apparatus for an endoscope according to claim 1, wherein at a position partway through the endoscope duct, the position being on the downstream side relative to a communication enabling region of the suction duct, a fitting to which a liquid supply member that supplies a liquid to the inside of the subject via the flow passage of endoscope duct is attached is provided.

* * * * *